United States Patent [19]

Wenman et al.

[11] Patent Number: 5,646,335

[45] Date of Patent: Jul. 8, 1997

[54] WICKLESS TEMPERATURE CONTROLLING APPARATUS AND METHOD FOR USE WITH PORE VOLUME AND SURFACE AREA ANALYZERS

[75] Inventors: Richard A. Wenman, Coral Springs, Fla.; Jon Fong, Manhattan Beach, Calif.

[73] Assignee: Coulter Corporation, Miami, Fla.

[21] Appl. No.: 519,054

[22] Filed: Aug. 24, 1995

[51] Int. Cl.$^6$ .................................................. G01N 15/08
[52] U.S. Cl. ............................................. 73/38; 73/865.5
[58] Field of Search ........................... 73/19.05, 23.27, 73/25.01, 304.11, 19.01, 863.11, 865.5, 38; 422/69; 220/414; 215/12.1, 12.2

[56] References Cited

U.S. PATENT DOCUMENTS

| | | | |
|---|---|---|---|
| 8,324 | 7/1851 | Norris | 215/12.1 |
| Re. 33,567 | 4/1991 | Killip et al. | 73/863.11 |
| 2,376,710 | 4/1945 | Maurer | 220/414 |
| 2,692,497 | 10/1954 | Van Nordstrand | 73/19.05 |
| 2,729,069 | 1/1956 | Innes | 73/19.05 |
| 3,059,478 | 10/1962 | Coggeshall et al. | 73/865.5 |
| 3,211,007 | 10/1965 | Atkins | 73/865.5 |
| 3,464,273 | 9/1969 | Hendrix et al. | 73/865.5 |
| 3,850,040 | 11/1974 | Orr, Jr. et al. | 73/865.5 |
| 3,934,117 | 1/1976 | Schladitz | 219/382 |
| 4,304,719 | 12/1981 | Wynne et al. | 260/314.5 |
| 4,332,290 | 6/1982 | Skala | 165/10 |
| 4,489,593 | 12/1984 | Pieters et al. | 73/38 |
| 4,560,288 | 12/1985 | Nara | 374/201 |
| 4,693,124 | 9/1987 | Killip et al. | 73/863.11 |
| 4,972,730 | 11/1990 | Camp et al. | 73/865.5 |
| 5,092,183 | 3/1992 | Leichnitz | 73/863.11 |
| 5,133,219 | 7/1992 | Camp | 73/865.5 |
| 5,228,703 | 7/1993 | White | 277/212 C |
| 5,235,184 | 8/1993 | Paulson | 250/238 |
| 5,237,836 | 8/1993 | Byrne et al. | 62/385 |
| 5,239,482 | 8/1993 | Akpt et al. | 364/497 |
| 5,360,743 | 11/1994 | Lowell | 436/5 |
| 5,408,864 | 4/1995 | Wenman | 73/38 |

OTHER PUBLICATIONS

Temperature–Compensated, Differential Tensimeter for Measuring Gas Adsorption by Low Surface Area Solids. Isao Suzuki, Rev. Sci. Instrum. 53(7), Jul. 1982, pp. 1061–1066 and Notes, p. 165.

British Standards Institute, BS 4359: Part 1: 1984, "Determination of the Specific Surface Area of Powders–Part I Recommendations for Gas Adsorption (BET) Methods".

Dollimore, D., et al., "The BET Method of Analysis of Gas Adsorption Data and Its Relevance to the Calculation of Surface Areas," *Surface Technology*, vol. 4, pp. 121–160 (1976).

*Primary Examiner*—Hezron E. Williams
*Assistant Examiner*—Jay L. Politzer
*Attorney, Agent, or Firm*—Mitchell E. Alter

[57] ABSTRACT

A wickless temperature controlling apparatus and method to analyze the characteristics of an adsorbent is provided. The apparatus provides a heat transfer between a cooling liquid and a sample vessel immersed in the cooling liquid and further provides a stabilized temperature to the sample vessel. The apparatus further comprises a thermal bridge between a saturation vapor pressure thermometer, which is also immersed in the cooling liquid, and the sample vessel to provide a uniform temperature between the thermometer and the vessel. The method to analyze the adsorbent utilizes the apparatus. In addition, the method includes a novel method of dosing an adsorptive gas to an adsorbent.

12 Claims, 4 Drawing Sheets

WICKLESS TEMPERATURE CONTROLLING APPARATUS AND METHOD FOR USE WITH PORE VOLUME AND SURFACE AREA ANALYZERS

BACKGROUND OF THE INVENTION

The measurement of morphological characteristics of solids, such as catalysts, catalyst supports, pigments, clays, minerals, pharmaceutics, and composite materials is an important aspect of analytical chemistry and quality control for manufacturing of numerous products.

For example, a very useful morphological characteristic of a solid is its surface area. One of the most widely used techniques for surface area determination is that of gas sorption. Gas sorption techniques utilize a theoretical model wherein the surface of a solid, the adsorbent, is characterized as being covered by a monolayer of closely packed molecules of an adsorbed gas. After adsorption on to the adsorbent, the condensed, relatively non-mobile gas phase is referred to as the adsorbate; whereas, the highly mobile gaseous phase is referred to as the adsorptive. If one can determine the amount, usually expressed in millimoles, of adsorbate which forms the monolayer, the area which is covered by the monolayer can be calculated from the product of the number of molecules in the monolayer and the cross sectional area of each molecule. In 1938 Branauer, EmBett, and Teller (*J. Am. Chem. Soc.*, Vol. 60, 2309) described a mathematical equation, referred to as the BET equation, for determining the amount of adsorbate in the monolayer from the adsorption isotherm of the adsorbate.

The adsorption isotherm is a plot of the amount of the adsorbate adsorbed on a solid adsorbent against either the relative pressure or the equilibrium pressure of the adsorbate at a constant temperature. In order to utilize the BET equation accurately to determine surface area, one must at least obtain a sufficient number of data points on the adsorption isotherm to be able to determine the point on the adsorption isotherm at which the "monolayer capacity" occurs. The "monolayer capacity" is a variable in the BET equation and represents the point on the adsorption isotherm, wherein a monolayer of closely packed adsorbed molecules is present at the surface of the adsorbent. Since the monolayer capacity generally occurred at prior to reaching an adsorptive relative pressure of 0.35, one desires to know the adsorption isotherm at least up to this value of relative pressure to be able to calculate the surface area from the BET equation. The adsorptive relative pressure is one way of expressing the equilibrium pressure of the adsorptive as a fraction of the pressure at which bulk condensation of the adsorptive occurs under any set of constant volume and temperature conditions. A concise review of the BET method appears in a publication by the British Standard Institution, BS 4359: Part 1: 1984, titled, "Determination of the Specific Surface Area of Powders-Part I Recommendations for Gas Adsorption (BET) Methods."

Adsorption isotherms can be determined by measuring the sample pressure and determining the amount of adsorbate adsorbed either with a volumetric or a gravimetric method. Use of this invention is applicable to both volumetric and gravimetric determinations of isotherms, although volumetric methods are preferred.

Three main volumetric techniques are in common use. These can be classified as static or fully equilibrated, continuous flow or quasi-equilibrated, and dynamic or chromatographic. Both the static and continuous flow techniques can be described as vacuum volumetric methods. However, in some publications, the dynamic technique has been described as continuous flow, although it does not use vacuum technology, but instead employs a non-adsorbing carrier gas and adsorptive mixture. For the purposes of this invention, the term "dynamic" is applied to all of the chromatographic types of sorption methods commonly used for rapid quality control analysis. As related to this invention, the static and continuous flow techniques are particularly applicable.

Volumetric methods conventionally employ a selected adsorptive at the most convenient temperature for adsorption. For example, when one uses the adsorptive nitrogen with an adsorbent sample to be tested, the adsorptive is cooled to a temperature of approximately 77K. The temperature of the adsorptive is provided by means of a liquid nitrogen bath in a dewar which is open to the atmosphere, and therefore the adsorptive has a boiling point equal to the environmental atmospheric pressure. By definition, the boiling point of a liquid is the temperature of the liquid at which its vapor pressure is equal to atmospheric pressure. When using liquid nitrogen, the boiling point is at a temperature at which the vapor pressure of the liquid nitrogen is equal to or slightly greater than the atmospheric pressure of the environment.

Consequently, since both the adsorbent and the adsorptive are cooled with the liquid nitrogen bath which is open to the atmosphere, the adsorptive gas and the adsorbent sample have a temperature equal to the boiling point of the liquid nitrogen bath. Because of variations in atmospheric pressure which affect the open dewar, or impurities in the liquid nitrogen bath which affect the saturation vapor pressure of the liquid nitrogen, the normal boiling point temperature of the liquid nitrogen changes very slightly from those reported at exactly one atmosphere pressure.

The reason that the adsorptive is cooled to the boiling point of liquid nitrogen is because it is recognized by those skilled in the art that the quantity of physically adsorbed gas at a given relative pressure (a fraction of saturation pressure) increases with decreasing temperature. Consequently, consistent with practical limits, the lowest most conveniently achieved temperature is chosen to provide maximum measurement sensitivity.

Volumetric devices typically consist of a gas storage unit and a vacuum source unit connected in parallel to a volumetric measuring device of known Volume $V_1$, referred to as the doser unit or the manifold unit. The doser unit can be connected alternately to either the vacuum unit or the gas storage unit by a series of valves. The doser unit in turn is connected in series through another valve to a sample unit, a chamber of known Volume $V_2$, which holds the solid sample to be tested. By manipulating the appropriate valves, the doser and sample units are evacuated and the evacuated doser is sealed off from the evacuated sample chamber. Nitrogen is permitted to slowly enter and fill the doser unit from the gas storage unit to a targeted pressure, at which time the valves are closed to seal off the doser, and the nitrogen pressure therein is measured. When a constant pressure $P_1$ in the doser is achieved, the valve separating the sample chamber and doser is opened allowing the adsorptive, typically $N_2$, in the doser to expand into the sample chamber.

The sample chamber and doser together define a third Volume $V_3$ (i.e. $V_1+V_2$). When the pressure in $V_3$ is constant, indicative of adsorption equilibrium, it is measured. This equilibrium pressure is used to calculate the total number of moles of $N_2$ that remains in the gas phase. The number of moles of $N_2$ adsorbed on the solid is equal to the number of moles of $N_2$ initially present in Volume $V_1$ of the doser, plus the number of moles of $N_2$ in the sample chamber defining Volume $V_2$ (the number of moles in Volume $V_1$ for the initial run is O, but increases with each successive run), less the number of moles of gaseous $N_2$ in Volume $V_3$, after equilibrium. The combined data of the amount of $N_2$ adsorbed at a particular equilibrium pressure constitutes a single point on the adsorption isotherm. The above procedure is repeated to obtain additional points on the adsorption isotherm. Each successive dose increases the pressure in the sample chamber until, at approximately atmospheric pressure, the sample becomes completely saturated with condensed $N_2$. At this saturation point, the majority of the $N_2$ condensation occurs on the sample contained in the sample holder. Conventional practice is to generate about 3 to 10 data points on the adsorption isotherm for surface area determinations. A detailed summary of this method is provided in the review paper, "The BET Method of Analysis of Gas Adsorption Data and Its Relevance to the Calculation of Surface Areas" by Dollimore, D., Spooner, P., and Turner, A. *Surface Technology*, Vol. 4, p. 121–160 (1976).

However, with manual dosing methods, exact target pressures are rarely achieved and several additional unwanted data points can be obtained. While the adsorptive gas is being dosed to the manifold in order to reach an estimated required pressure, an increase above the pressure desired can be obtained. If this higher than required pressure is dosed to the sample, significant loss of operational range can result if too much gas is adsorbed. It is normal practice to open the nitrogen gas adsorptive valve very carefully. This valve typically is capable of supplying nitrogen to higher than atmospheric pressure. If an increase above the pressure desired does occur, then it must be removed by judicious opening of the vacuum valve, before adsorption. Additional pressure stabilizing time is always required and typically is equal to one or two minutes. This time is in addition to the sorption equilibration time.

A capillary method having a continuous flow of the adsorptive is disclosed in U.S. Pat. No. 2,729,969 to Innes. Innes teaches a method for the measurement of surface areas which comprises introducing nitrogen gas at a constant flow rate into an evacuated system containing a weighed sample amount which is cooled to −195 C., measuring the time required for the vacuum in the evacuated system to decrease from 29.6" to 23.7" of mercury and calculating from the time required the surface area of the material. Innes further teaches that due to impurities present in the liquid nitrogen cooling bath, the bath temperature is somewhat higher than the boiling point of pure nitrogen. As a result, the saturation vapor pressure is slightly above one atmosphere. It has been reported elsewhere that dissolved impurities usually increase the bath temperature sufficiently to cause the vapor pressure of pure liquid nitrogen in the sample cell to increase by 10 to 20 mm Hg above ambient pressure. However, the Innes method suffers from environmental induced flow rate fluctuations and imprecise equilibrium pressure conditions, which affect the accuracy of measurement.

U.S. Pat. No. 4,489,593 to Pieters, et al. discloses using an adsorptive at a temperature at which the adsorptive condenses at approximately one atmosphere pressure and introducing the adsorptive into the sample holder containing the substance to be analyzed at a constant flow rate. By controlling the mass flow rate to be not greater than the equilibration rate of adsorption, the pressure established, at any given time during the introduction of the adsorptive, will be equilibrium pressure. This is significant because the adsorption isotherm is a plot of the amount of adsorptive adsorbed at a given equilibrium pressure. Consequently the determination of the adsorption isotherm is simplified.

U.S. Pat. No. 4,972,730 is directed to the determination of the saturation vapor pressure after dosing and measurement of the adsorption isotherm has been completed. The sample is deliberately overdosed to cause bulk condensation of adsorbate in the sample tube. This condensation occurs exterior to the sample pores because the pores have already been filled with liquid gas during the measurement of the adsorption isotherm. At the point when the sample pores are full, the addition of further gas must condense as bulk liquid. Measurement of the sample pressure after this overdose gives an accurate determination of the saturation vapor pressure at the sample temperature (at this moment in time only). The saturation vapor value recorded with this sample tube vapor pressure thermometer is used for the calculation of relative pressure values during the subsequent measurement of the desorption isotherm. However, the sample tube vapor pressure thermometer suffers from thermal currents in the liquid nitrogen bath.

In each of the methods described above, it is important to have a non fluctuating temperature because uncontrolled changes in temperature create uncontrolled changes in saturation vapor pressure. This can lead to errors in determining the amount of gas adsorbed by the sample.

Several prior art devices have been developed to maintain gases at a constant temperature within a vessel. In one device, the cryogenic liquid is contained within a dewar flask, and the entire flask is raised at the same rate that evaporation occurs, thereby keeping the level of the liquid at the same height with respect to the vessel. The major disadvantage to this device is that, as the dewar flask is raised, it surrounds more and more of the previously exposed portion of the vessel and traps the cold gas molecules as they evaporate from the cryogenic liquid, thereby shifting the gradient and creating uncontrolled temperature and pressure changes within the vessel.

Another device, described in U.S. Pat. No. 3,850,040, transfers fresh liquid to the dewar flask at the same rate that evaporation occurs, so that the height of the liquid remains at a constant level. In this device the temperature gradient does not shift. The major disadvantage to this device is that, in humid climate, ice can accumulate within the valves and seals on the apparatus used to pump the liquid from the reservoir to the dewar flask and can cause the device to fail.

An apparatus for use with a scientific instrument such as a pore volume and surface area analyzer is disclosed in Killip et al. U.S. Pat. No. 4,693,124. Killip et al. teach maintaining gases within the sample vessel at constant temperature, by providing an apparatus which maintains a liquid at a fixed height surrounding the gas-containing vessel. Killip et al. teach maintaining a constant temperature within a vessel immersed in a liquid by surrounding a portion of the vessel, extending above the surface of the liquid, with a wick. The wick conducts liquid up to a predetermined point on the vessel and maintains the liquid at that point, regardless of changes in the level of the liquid due to evaporation.

Desorption isotherms are important because various mathematical equations have been developed to enable one skilled in the art to determine certain morphological characteristics of solids. More specifically, adsorption, as well as desorption isotherms enable one to calculate the pore size distribution of a solid sample from the data embodied therein. A desorption isotherm is a plot of the amount of a preadsorbed gaseous material, the desorbate, desorbed from a solid against the equilibrium pressure or relative pressure of the desorbate at a constant temperature. After desorption from a solid sample, the desorbent, the gas is referred to as the desorptive. The desorption isotherm differs from the adsorption isotherm in that it is constructed starting with a solid, saturated with the desorbate, and gradually reducing the pressure over the solid to near absolute vacuum. In contrast, the adsorption isotherm starts with an evacuated solid sample and increases the pressure of a gaseous adsorptive in contact therewith sample saturation is reached. The adsorption and desorption isotherms are collectively known as the isotherm.

Gas-solid interaction can cause at least a portion of the desorption path of the sorption isotherm to lie higher on the isotherm plot than the adsorption path. The failure of the desorption path to duplicate the adsorption path of the isotherm is referred to as hysteresis. The two most common forms of hysteresis are closed loop and open loop. In the closed loop hysteresis behavior, the desorption path of the isotherm eventually rejoins the adsorption path at some low relative pressure. Closed loop hysteresis normally is associated with porosity in the sample being tested.

For example, at the start of the desorption isotherm, the pores of the sample are saturated and filled with the desorbate. As desorption occurs, capillary action delays desorption of the desorbate present within the pores, such that a lower pressure is required to evacuate the pores relative to the pressure which initiated the filling of the pores during adsorption. This delay is expressed as closed loop hysteresis behavior of the sorption isotherm. Open loop hysteresis is characterized by the failure of the desorption path of the isotherm to rejoin with the adsorption path. Open loop hysteresis usually is associated with some measurable amount of irreversible adsorption, which typically occurs when the gas reacts with the solid sample upon adsorption, conventionally referred to as chemisorption. Consequently on desorption, less material will desorb than was initially adsorbed, giving rise to an open loop in the sorption isotherm.

By intentionally inducing chemisorption, much can be learned about the surface of the solid sample. For example, chemisorption can be employed to determine the percent dispersion and surface area of microscopic particles of a catalyst deposited on a support by employing a gaseous adsorbate which will undergo chemisorption with the catalyst particles but not the support.

Other information in the substantially complete sorption isotherm permits the determination of total pore volume, average pore size, and pore shape, for example, slits versus cylindrical pores.

The above discussion highlights only a few of the incentives for obtaining substantially complete pictures of the entire sorption isotherm rather than narrow segments thereof, and any method or device capable of producing substantially complete sorption isotherms quickly and accurately possesses substantial advantages.

In view of the above, it is evident that there has been a continuing search for a simple device that maintains an evaporating liquid at a constant temperature in order to keep the gases within a vessel immersed in the liquid at a constant temperature. The present invention was developed in response to this search.

SUMMARY OF INVENTION

The present invention provides a temperature controlling apparatus and method for use with surface area and pore volume analyzers. The apparatus comprises a container of volatile cooling liquid, such as a dewar flask filled with liquid nitrogen, a sample vessel which contains a sample to be analyzed, and a temperature controlling means for providing a heat transfer between the cooling liquid and the vessel and further providing a stabilized temperature to the vessel. The sample vessel is immersed in the cooling liquid, but extends above the surface of the cooling liquid. The means remains immersed in the volatile cooling liquid without being exposed to the atmosphere regardless of changes in the level of the cooling liquid.

Once immersed into the cooling liquid, the temperature controlling means remains stationary and is wickless. More specifically, once the sample vessel is attached to the means, it does not move in the cooling liquid. Moreover, the means does not conduct the cooling liquid positioned in the container from a location at or below the surface of the liquid in the container to a point along the side of the vessel which is above the surface of the liquid.

The apparatus further comprises a thermal bridge between a saturation vapor pressure thermometer, which is also immersed in the cooling liquid, and the sample vessel to provide a uniform temperature between the thermometer and the vessel.

The method of this invention provides a method of determining a sorption isotherm comprising the steps of inserting a sample to be analyzed into a sample vessel which contains an exterior means that remains below the surface of the cooling liquid during analysis of the sample; providing a heat transfer between a cooling liquid and the sample vessel and further providing a stabilized temperature to the vessel through the exterior means; immersing the vessel in a container of volatile cooling liquid with a portion of the vessel extending above the surface of the cooling liquid; dosing an amount of absorbent gas to the sample; and constructing a sorption isotherm from the amount of said adsorptive gas that is condensed on the sample.

In a preferred embodiment, the amount of gas used to dose the sample is determined from a previously measured sorption measurement of a sample that is the same as the sample being analyzed.

The apparatus and method are useful for providing accurate and reproducible pore size determinations.

DETAILED DESCRIPTION OF TEE INVENTION

The present invention is related to an apparatus and method to improve gas sorption measurements. Preferably, the apparatus and method provide improved pore size distribution measurements. The apparatus and method can be used for instruments that employ static and continuous flow techniques, and other vacuum volumetric methods. The apparatus and method of the present invention are applicable in an adsorption mode, in a desorption mode, or a combination of the two, wherein the adsorption mode is followed by the desorption mode.

The adsorption mode is conducted using a substance existing initially as a gas vapor, referred to therein as the adsorptive, and a solid sample, referred to herein as the adsorbent or sample. During the course of the adsorption mode, the adsorptive is adsorbed by the adsorbent. Thereafter, the adsorptive that is adsorbed is referred to as the adsorbate. The identity of the adsorptive will vary depending on whether the nature of the adsorption is intended and controlled to be physical, or physical and chemical. It is known that the adsorption phenomena can be the result of a physical or a physical and chemical process depending on the system involved and the temperature employed. Physical adsorption, frequently referred to as van de Waals' adsorption, is the result of a relatively weak interaction between solid and gas. One of the characteristics of this type of adsorption is that all the gas adsorbed by the solid can be removed therefrom by evacuation at about the same temperature at which it was adsorbed. For physical adsorption, the adsorptive is selected to be chemically inert with respect to the adsorbent.

Representative examples of adsorptives conventionally employed for physical adsorption include nitrogen, argon, krypton, oxygen, xenon, neon, helium, carbon dioxide and hydrocarbons, such as methane, butane, hexane and benzene. The adsorptive gas can comprise a component gas and an inert carrier gas. Preferably the adsorptive gas comprises at least 80 percent of a single component gas and less than 20 percent of a carrier gas. Most preferably, the adsorptive gas comprises a single gas without a carrier gas.

Since the quantity of physically adsorbed gas or vapor at a given pressure increases with decreasing temperature, the adsorptive typically is selected so that it will liquify at very low temperatures. These low temperatures correspond to the boiling points at atmospheric pressure of conventionally employed adsorbates which are noted in the following table.

TABLE 1

|  | Standard Boiling Point at 1 atmosphere (K) |
| --- | --- |
| Nitrogen | 77.35 |
| Argon | 87.45 |
| Krypton | 120.45 |
| Oxygen | 90.18 |
| Xenon | 166.05 |
| Neon | 27.10 |
| Helium | 4.2 |
| Air (21% $O_2$) | 78.8 |
| Methane | 111.66 |
| Butane | 272.5 |
| Hexane | 341.7 |
| Benzene | 353.1 |
| Carbon dioxide | 194.5 |

Before determining the amount of adsorptive adsorbed by a sample, the sample is placed in a sample chamber and cleansed of impurities by removing adsorbed atmospheric gases, such as nitrogen, oxygen, and water vapor. This process is referred to as outgassing. The process is achieved by conventional methods known to those skilled in the art. Examples of such methods are described in Orr, C. and Dallavalle, J., "Fine Particle Measurement" Macmillan Co., p. 164–204 (1960). One such disclosed example includes heating the sample in a vacuum at temperatures of about 110° to about 600° C. for a period of from about 4 to about 12 hours. The sample weight and density can also be determined in accordance with conventional methods before the sample is contacted with the adsorptive.

Thereafter and in accordance with procedures known to those skilled in the art, the overall volume of the sample chamber is determined. In addition, the volume of the sample in the chamber is determined by procedures known to those skilled in the art and designated as the "dead space"; whereas, the remaining volume of the sample chamber and the piping between it and the manifold doser is designated as the "free space." Typically, helium gas is chosen to be used to determine the dead space, because it is substantially inert and also because there is no appreciable adsorption of helium by the sample materials at the cryogenic temperature of the sample.

Using methods known to those skilled in the art, the free space is determined by the conventional method of pre-charging the doser unit to a predetermined pressure, and then permitting the helium in the doser unit to expand into the sample chamber. The reduction in pressure in the doser unit can be converted by those skilled in the art by use of standard computation techniques to a value which represents a corresponding number of cubic centimeters of helium gas, taken at the reference temperature and pressure.

After the free space of the sample chamber has been determined, sample analysis is commenced. In traditional static and continuous flow techniques, the adsorptive nitrogen gas and adsorbent are maintained at approximately the boiling point temperature of the adsorptive and at a saturation vapor pressure of one atmosphere. As appreciated by those skilled in the art, the temperature of the adsorptive in the conventional isotherm measurement can change slightly due to environmental conditions in the liquid nitrogen bath. Table 2 demonstrates the gradual increase in temperature of the liquid nitrogen bath that typically occurs due to oxygen, carbon dioxide and water vapor contaminants which are from the environment.

TABLE 2

| Time-Temperature of a Liquid Nitrogen Bath | | | |
| --- | --- | --- | --- |
| 0 min. | 77.103K | 90 min. | 77.128K |
| 5 | 77.106 | 95 | 77.143 |
| 10 | 77.099 | 100 | 77.155 |
| 15 | 77.079 | 105 | 77.130 |
| 20 | 77.090 | 110 | 77.121 |
| 25 | 77.086 | 115 | 77.130 |
| 30 | 77.095 | 120 | 77.129 |
| 35 | 77.104 | 125 | 77.137 |
| 40 | 77.077 | 130 | 77.128 |
| 45 | 77.083 | 135 | 77.144 |
| 50 | 77.101 | 140 | 77.154 |
| 55 | 77.071 | 145 | 77.162 |
| 60 | 77.104 | 150 | 77.171 |
| 65 | 77.107 | 155 | 77.183 |
| 70 | 77.112 | 160 | 77.200 |
| 75 | 77.114 | 165 | 77.208 |
| 80 | 77.122 | 170 | 77.225 |
| 85 | 77.124 | 175 | 77.218 |
|  |  | 180 | 77.227 |

The fluctuations in the temperature are attributed to several factors including impurities which occur because the dewar is open to the atmosphere. The fluctuations in temperature causes thermal currents within the liquid nitrogen bath. As noted, the increase in temperature of the liquid nitrogen bath has a long term affect of increasing approximately 0.12K over a three hour period. During the short term intervals, there are temperature variations, which although are small, they can significantly affect surface area determinations and especially pore size determinations.

The temperatures noted above were obtained in an open dewar containing liquid nitrogen. The liquid nitrogen was not replenished during the measurement. The boiling point of the liquid nitrogen was determined to be at 769.3 mm Hg pressure. In addition, the boiling point of fresh nitrogen was observed to be approximately 77.10K. The difference between the observed boiling point temperature and the standard textbook value reported, might be attributed to the accuracy of the temperature probe and environmental atmospheric conditions.

As appreciated by one skilled in the art, the saturation vapor pressure is determined by prior art methods so that sorption measurements can be made at relative pressures from 0 to 1. To determine the saturation vapor pressure, the prior art supplies a predetermined high pressure of the adsorptive into a vapor pressure thermometer. Thereafter, the vapor pressure thermometer is placed into a cooling medium, which causes a small amount of the gaseous adsorptive to condense; thereby establishing the saturation vapor pressure of the adsorptive at a temperature which is also the temperature at which subsequent analysis of the sample chamber occurs.

As taught by U.S. Pat. No. 3,850,040 to Orr, Jr. et al., when using nitrogen as the adsorptive, the saturation vapor pressure is determined by precharging the vapor pressure thermometer with nitrogen to a predetermined high pressure, such as 850 mm Hg, and thereafter placing the vapor pressure thermometer into an open dewar filled with liquid nitrogen. The lowering of the temperature of the vapor pressure thermometer causes a small amount of the gaseous nitrogen in the vapor pressure thermometer to condense, thereby establishing the saturation vapor pressure of nitrogen at a temperature which also is used for subsequent analysis of the sample chamber. It will also be understood that this saturation vapor pressure for nitrogen can be used to calculate the saturation vapor pressure for another gas in the event that such other gas is used in place of nitrogen for the gas sorption analysis.

By using similar principles, the saturation temperature can be determined. To determine the saturation temperature, a vapor pressure thermometer is precharged with the adsorptive to a predetermined high pressure. Thereafter, the vapor pressure thermometer is cooled by the cooling medium. When the adsorptive is at equilibrium between the vapor and liquid phases, the temperature is measured, which is also the saturation temperature used in subsequent analysis of the sample chamber.

The identity of the adsorbent or sample can be any solid sought to be analyzed for its morphological characteristics, such as surface area. The apparatus and method described herein are applicable to a sample having a surface area of typically from about 0.001 to about 2000 $m^2/g$, preferably from about 0.05 to about 1500 $m^2/g$, and most preferably from about 0.5 to about 1000 $m^2/g$; and pore size radii of typically from about 0.35 to about 300 nanometers, preferably from about 0.5 to about 100 nanometers, and most preferably from about 0.5 to about 50 nanometers.

The apparatus of the present invention is used to provide a stabilized temperature to the sample vessel. A stabilized temperature means that the sample temperature does not fluctuate during short term intervals due to thermal currents. As previously noted in Table 2, the cooling liquid temperature has short term positive and negative fluctuations of temperature from the previous reading throughout a typical period of analysis. However, the apparatus provides a stabilized temperature to the sample vessel which is unaffected by the heat transfer from the: 1) adsorption and desorption process, 2) atmosphere to the sample by the vessel, or 3) gas dose. Any one of these three items can cause short term differences in temperature to the sample vessel. Notwithstanding, it is appreciated by those skilled in the art, that the sample temperature will be affected by the long term changes of the cooling liquid temperature.

Figure 1:
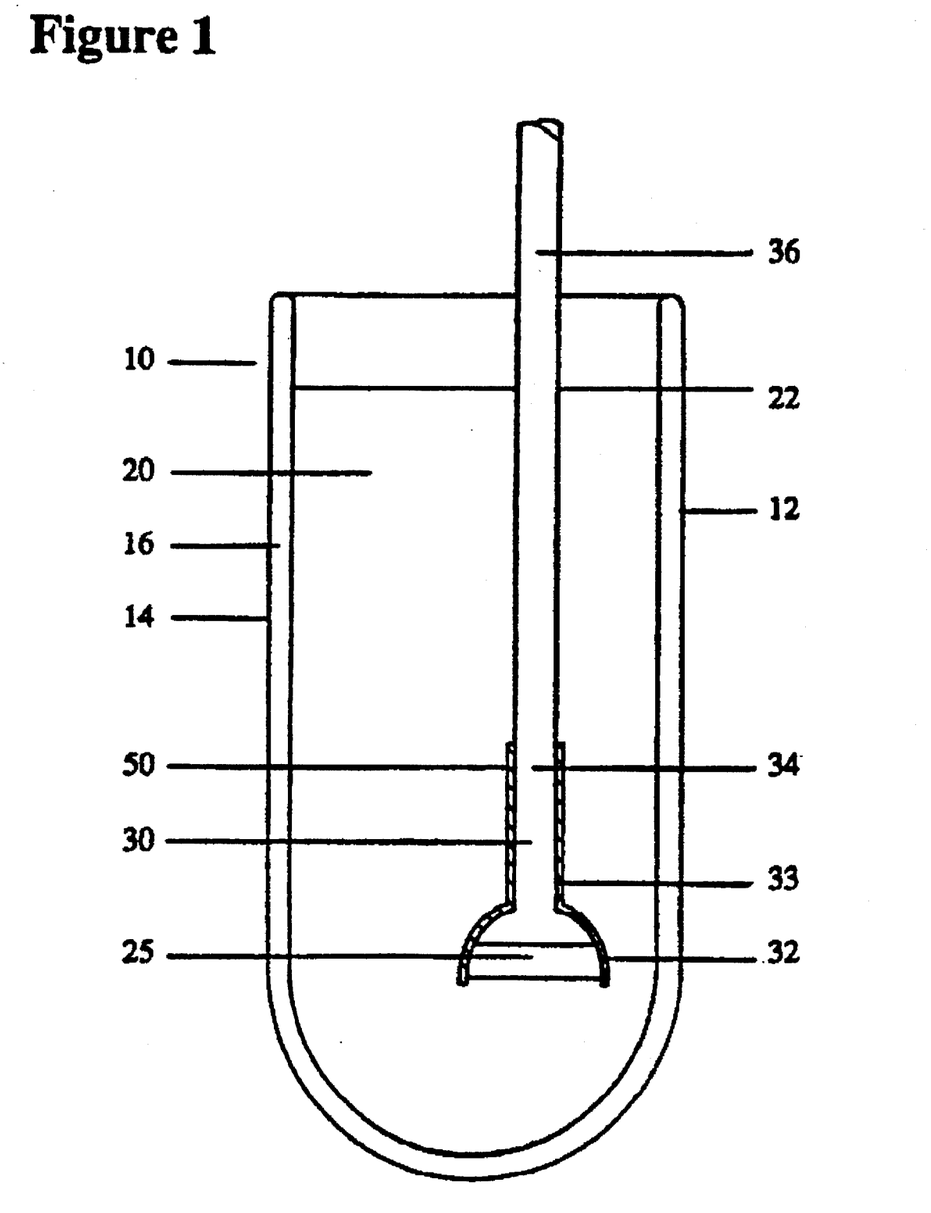
FIG. 1 is a vertical cross section view of the temperature controlling apparatus embodying the present invention.

The apparatus of the present invention that is depicted in the drawings. Referring now in more detail to the drawings, in which like reference numerals refer to like parts throughout the several views, FIG. 1 shows a temperature controlling apparatus 10 embodying the present invention. The apparatus includes a container 12, preferably an insulated container such as a dewar flask, having an external wall 14 surrounding a vacuum chamber 16. It will be understood that any container capable of withstanding extremely cold temperature of the particular liquid to be placed therein, can be substituted for the dewar flask, depending on the nature of the liquid to be held in the container.

The container 12 is partially filled with a liquid 20, preferably an evaporating cooling liquid such as liquid nitrogen. Liquid nitrogen is preferred since it will provide a very cold temperature medium to surround a vessel 30 at very low temperatures. The uppermost level of the liquid defines a horizontal surface 22 from which evaporating liquid or vapor escapes.

A test sample 25 is place into a vessel 30 for analysis. The vessel comprises a size and shape capable of being inserted within the liquid filled container 12. The sample containing vessel 30 is then immersed in the liquid 20 in the container 12. The preferred vessel 30 of the present invention includes a flat bottom flask 32 at the lowermost end of the vessel having an opening 33 connected to an elongated tube 34 extending upwardly from the flask. The preferred vessel 30 thus can be a flat bottomed vessel of the type commonly used in scientific laboratories. For some applications, such as dynamic or chromatographic flow sample analysis, the sample vessel may be a U-shaped tube. The entire vessel is made of a substance capable of withstanding the temperature of the liquid into which it is immersed. Preferably, the vessel is made of a substance capable of withstanding extremely hot or cold temperature, such as PYREX® brand glassware.

The flat bottom flask 32 of the sample containing vessel 30 is normally immersed below the surface 22 of the liquid 20 as shown in FIG. 1. The elongated tube 34 can also be immersed partially below the surface 22 of the liquid and is removably attached at it uppermost end 36 to an analytical scientific instrument (not shown). The attached analytical instrument can be, for example, a pore volume and surface area analyzer such as a Coulter Corporation SA 3100 analyzer, manufactured by Coulter Corporation, Miami, Fla. The pore volume and surface area of the sample 25 contained within the sample flask 32 of the vessel 30 is determined according to methods known to those skilled in the art.

In accordance with conventional volumetric gas sorption analytical procedures, the volume of the sample holder is selected to be from about 1 to about 20, preferably 1 to 10, and more preferably 1 to 5 times the volume of the sample. The size of the sample holder contributes to an accurate determination of the free space used for both adsorption and desorption; and to minimize error which can be introduced by the gas volume value at the liquid bath-air interface by fluctuations in the liquid nitrogen level. If the sample holder is too large, the accuracy of measurement will be adversely affected.

AS shown in FIG. 1, the elongated tube 34 of the vessel 30 is surrounded by a sleeve or collar 50. The collar 50 extends from bottom of the elongated tube 34 to a predetermined point beneath the surface 22 of the liquid 20.

Examples of a possible collar would include a solid metal collar, wire wound around the flat bottom flask 32, and braided wire around the flat bottom flask. In a preferred embodiment, not shown, the collar 50 covers the flat bottom flask 32. More specifically, the collar 50 covers the entire lower portion of the flat bottom flask 32 and a portion of the elongated tube 34, providing it remains below the surface 22 of the cooling liquid 20.

The top of the collar 50 should be always remain lower than the surface 22 of the liquid 20. Therefore, the length of the collar 50 should take into account the amount of evaporation which will occur during the analytical testing of the sample in the vessel. The collar 50 is comprised of a heat conductive material which will provide an efficient heat transfer between the liquid 20 and the test sample 25. Examples of such material would include metals such as copper, silver, gold or alloys metals such as steel and brass.

The collar 50 and the flat bottom flask 32 of the sample containing vessel 30 can be constructed of the same material, providing that the elongated tube 34 that is above the liquid level 22 is of a non heat conductive material. More specifically, the collar 50, and flask 32 can be a single fabricated apparatus providing that it is connected to a elongated tube 34 which is a thermal insulator so that temperature from the atmosphere above the liquid level 22 is not transferred into the liquid 20.

The collar 50 is impervious to the liquid 20 and should fit around the flask 32 to enable an efficient heat transfer from the adsorptive gas and the adsorbent sample to the liquid nitrogen 20. Since liquid nitrogen acts as an insulating material, it is preferred to have a minimum amount of liquid nitrogen between the collar 50 and the flask 32. The collar 50 can be of varying thickness. The function of the collar 50 is to provide an efficient heat transfer between the liquid 20 to the test sample 25. In addition, the collar 50 provides a heat reservoir to eliminate the temperature fluctuations caused by the thermal currents in the liquid 20. Preferably, the collar has a thickness of approximately 0.5 millimeters. As appreciated by those skilled in the art, the thickness can vary dependent upon the mass of the collar.

The adsorption process is exothermic, and this additional heat increases the convection currents that exists in the liquid nitrogen bath used to cool the sample. A 0.25K difference causes a significant effect upon the saturation vapor pressure and the apparent pore size. The saturation vapor pressure of nitrogen changes by approximately 22 mm Hg for each 0.25K change in temperature from 77.4K. For example, the apparent Kelvin radius calculated at a relative pressure of 0.995 changes from 187 nanometers to 27.5 nanometers if the temperature change increase by 0.25K.

Figure 4:
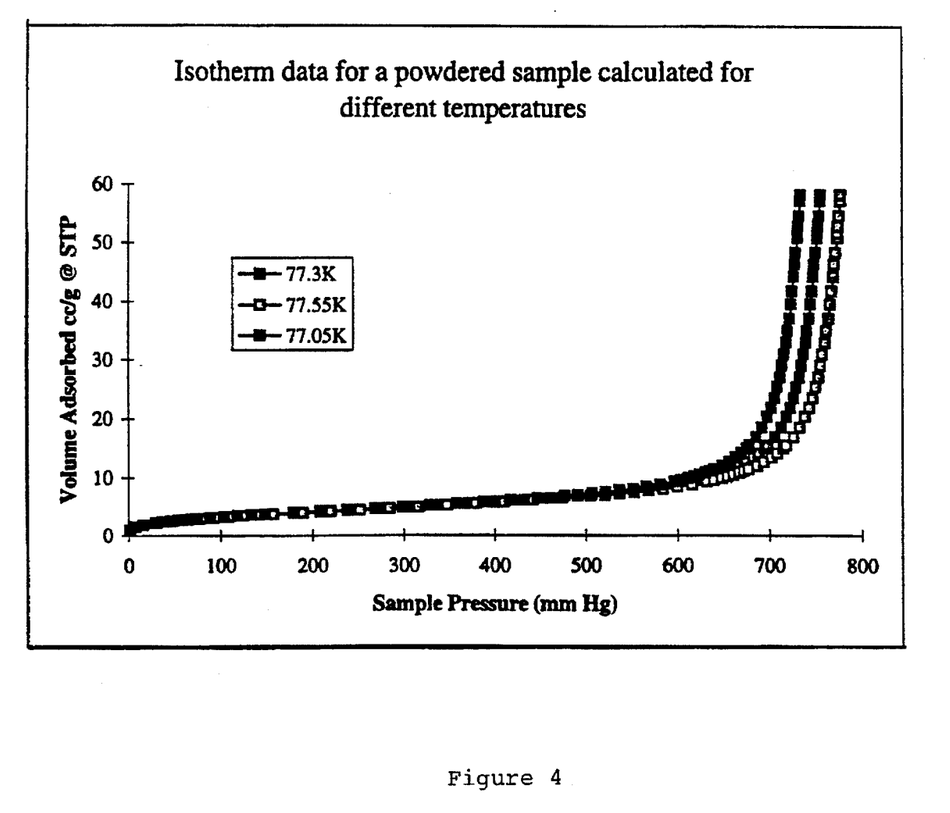
FIG. 4 is an isotherm plot which is constructed with sample pressure rather than relative pressure.

An isotherm plot which is constructed with sample pressure rather than relative pressure illustrates the effect of small temperature errors on the sample pressure. These differences can create substantial errors in the pore size determinations. This is graphically shown in FIG. 4 which depicts three isotherms which are developed with slightly different sample temperatures. Consequently, the adsorbent temperature must be accurately known for determining surface area and most importantly for pore size determinations.

Figure 2:
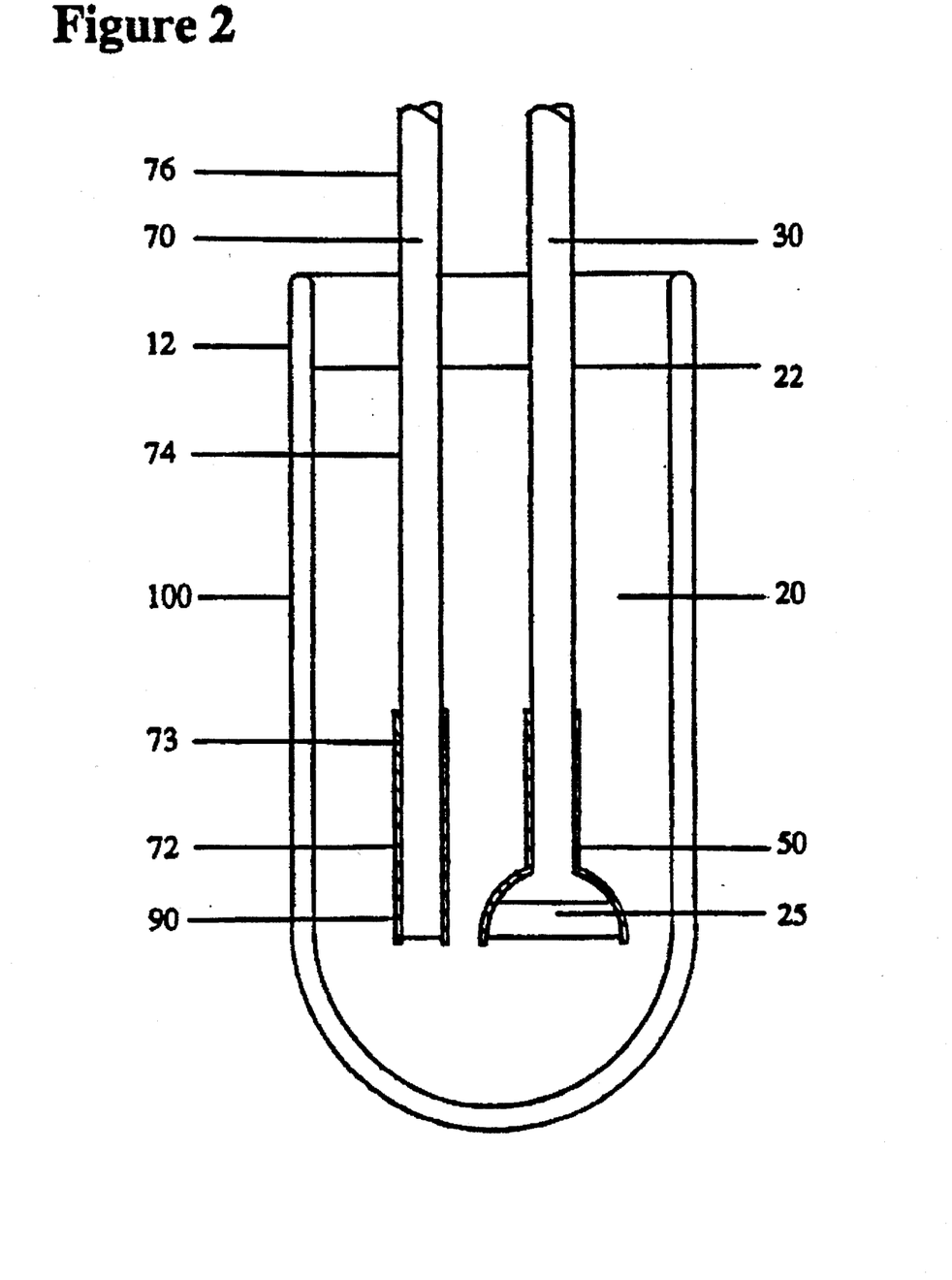
FIG. 2 is a vertical cross section view of a second embodiment of the present invention.

In a second embodiment of the present invention, FIG. 2 shows a temperature controlling apparatus 100 embodying the present invention. FIG. 2 is a vertical cross-sectional view similar to that shown in FIG. 1 for the first embodiment. In the second embodiment, the container 12, liquid 20, sample 25, vessel 30 and collar 50 are similar to that for the first embodiment shown in FIG. 1, however a saturation vapor pressure thermometer tube 70 is added to provide an accurate reading of the temperature during the analysis.

The saturation vapor pressure thermometer tube 70 comprises a tube of a size and shape capable of being inserted within the liquid filled container 12. The preferred saturation vapor pressure tube 70 of the present invention includes flat bottom cylinder 72 at the lowermost end of the tube having an opening 73 connected to an elongated tube 74 extending upwardly from the cylinder. However, the preferred saturation vapor pressure thermometer tube 70 can have a rounded or flat bottomed and is of the type commonly used in scientific laboratories. The entire tube is made of a substance capable of withstanding the temperature of the liquid into which it is immersed. Preferably, the tube is made of a substance capable of withstanding extremely hot or cold temperature, such as PYREX® brand glassware.

The tube 70 is then immersed in the liquid 20 in the container 12. As shown in FIG. 2, the elongated tube 74 is also immersed partially below the surface 22 of the liquid 20 and is removably attached at it uppermost end 76 to an analytical scientific instrument (not shown). As further shown in FIG. 2, the cylinder 72 of the vessel 70 is surrounded by a sleeve or collar 90. The collar 90 extends from bottom of the cylinder 72 to a predetermined point beneath the surface 22 of the liquid 20. In a more preferred embodiment, not shown, the collar 90, covers the bottom of the cylinder 72. More specifically, the collar 90 would cover the entire lower portion of the flat bottom cylinder 72 and a portion of the elongated tube 74, providing it remains below the surface 22 of the cooling liquid 20. The top of the collar 90 should be always remain lower than the surface 22 of the liquid 20. Therefore, the length of the collar 90 should take into account the amount of evaporation which will occur during the analytical testing of the sample in the vessel. The collar 90 is comprised of a heat conductive material which will provide an efficient heat transfer between the liquid 20 and the adsorptive gas. Examples of such material would include metals such as copper, silver, gold or alloys metals such as steel and brass.

The collar 90 and the cylinder 72 of the saturation vapor pressure thermometer 70 can be constructed of the same material, providing that the elongated tube 74 that is above the liquid level 22 is of a non heat conductive material. More specifically, the collar 90, and cylinder 72 can be a single fabricated apparatus providing that it is connected to a elongated tube 74 which is a thermal insulator so that temperature from the atmosphere above the liquid level 22 is not transferred into the liquid 20.

The collar 90 is impervious to the liquid 20 and should fit around the cylinder 72 to have an efficient heat transfer between the adsorptive gas and the liquid nitrogen 20. Since liquid nitrogen acts as an insulating material, it is preferred to have a minimum amount of liquid nitrogen between the collar 90 and the cylinder 72. The collar 90 can be of varying thickness. The function of the collar 90 is to provide an efficient heat transfer from the liquid 20 to the adsorptive gas in the tube 70 and to provide a heat reservoir to eliminate the temperature fluctuations of the adsorptive gas in the tube 70 caused by the thermal currents in the liquid 20. Preferably, the collar has a thickness of approximately 0.5 millimeters. As appreciated by those skilled in the art, the thickness can vary dependent upon the mass of the collar.

Figure 3:
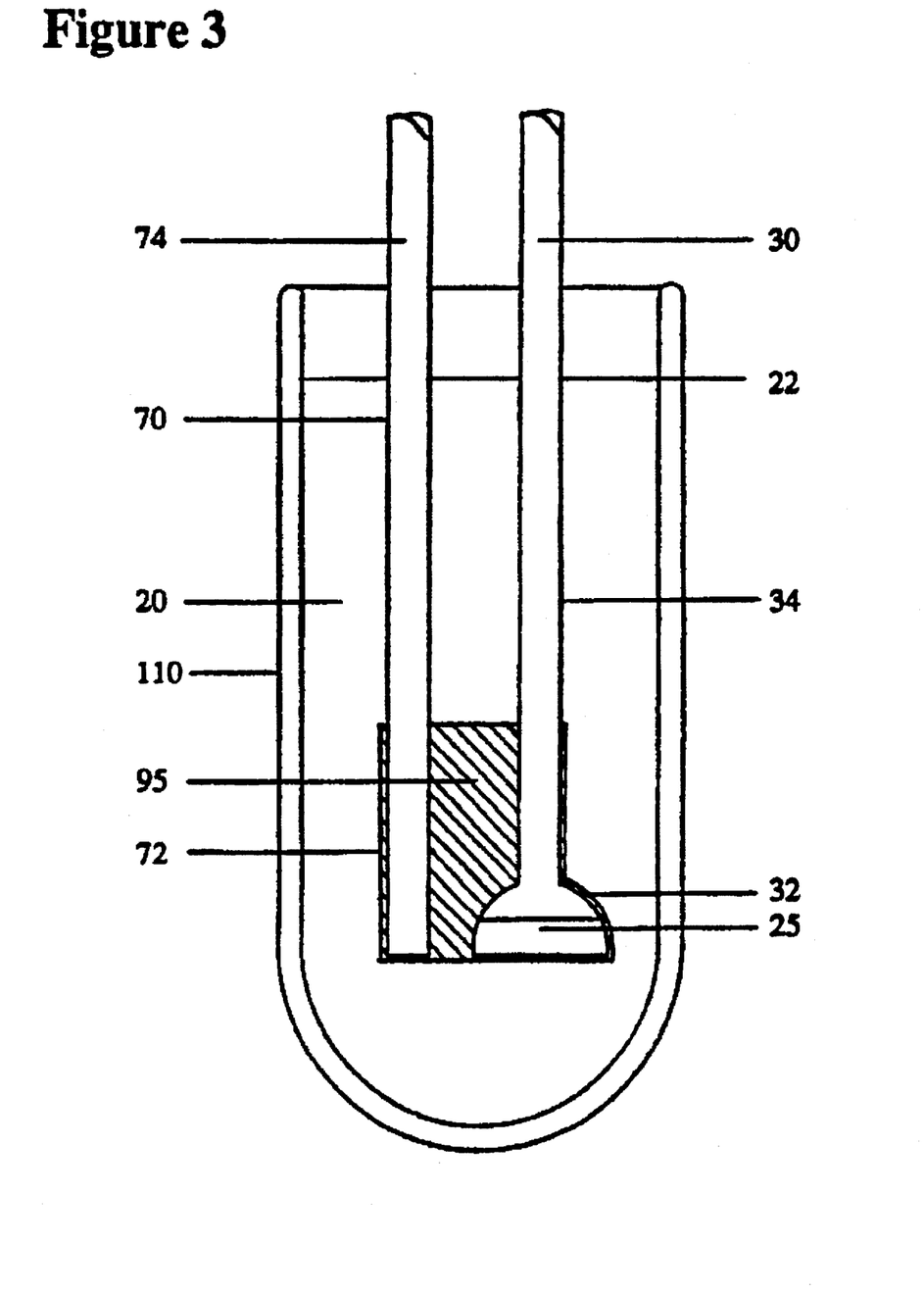
FIG. 3 is a vertical cross section view of a third embodiment of the present invention.

In a third embodiment of the present invention, FIG. 3 shows a temperature controlling apparatus 110 embodying the present invention. FIG. 3 is a vertical cross-sectional view similar to that shown in FIG. 2 for the second embodiment. In the third embodiment, the sample vessel 30 and the saturation vapor pressure thermometer 70 are similar to that shown in FIG. 2 for the second embodiment. In the third embodiment, the sample vessel 30 and saturation vapor pressure thermometer 70 are thermally connected to each other to provide a consistent temperature for the vessel 30 and the thermometer 70. More specifically, the sample vessel 30 and the saturation vapor pressure thermometer 70 have a heat bridge 95 that is formed of a material which surrounds the vessel 30 and the thermometer 70.

The top of the bridge 95 should be always remain lower than the surface 22 of the liquid 20. Therefore, the height of the bridge 95 should take into account the amount of evaporation which will occur during the analytical testing of the sample in the vessel. The bridge 95 is comprised of a heat conductive material which will provide an efficient heat transfer among the liquid 20, the vessel 30 and the thermometer 70. The bridge 95 also provides a further means to stabilize the temperature fluctuations which occur in the vessel and thermometer. In addition, the bridge provides still a further means by which the vessel and thermometer have similar reportable temperatures. Examples of material that can be used to construct the bridge 95 would include metals such as copper, silver, gold or alloys metals such as steel and brass.

The bridge is constructed so that the flat bottom flask 32 of the sample containing vessel 30, and cylinder 72 of the saturation vapor pressure thermometer can be inserted into the bridge in preparation for the sample analysis and withdrawn from the bridge 95 after analysis has been completed. Examples of a possible bridge would include a thermal conductive material which sandwiches the sample vessel 30 and cylinder 72 in the middle. Alternatively, the bridge 95, the flat bottom flask 32 of the sample containing vessel 30, and cylinder 72 of the saturation vapor pressure thermometer can be constructed of the same material, providing that the bridge remains below the surface of the liquid level 22. More specifically, the bridge 95, the flat bottom flask 32 of the sample containing vessel 30, and cylinder 72 of the saturation vapor pressure thermometer can be a single fabricated apparatus. In such case, the elongated tube 34 and the elongated tube 74 should be a thermal insulator so that temperature from the atmosphere above the liquid level 22 is not transferred into the liquid 20.

The bridge 95 can be of varying thickness. The function of the bridge 95 is to provide a heat reservoir to eliminate the temperature fluctuations of the test sample 25 and the saturation vapor pressure thermometer 70. In addition, the bridge provides a further means by which the vessel and thermometer have similar reportable temperatures. Preferably, the collar has a thickness of approximately 0.5 millimeters. As appreciated by those skilled in the art, the thickness can vary dependent upon the mass of the collar.

Sorption analysis is performed at one or more relative pressure points from 0 to 1. The sorption analysis can be performed at fixed pressure points equivalent to the required relative pressures, by the incremental increase of pressure from the pressure source. Although these fixed pressure points can be calculated from the predetermined relative pressure points, relative to the saturation pressure, this is not required by this invention. More specifically, one can choose relative pressures of 0.04, 0.08, 0.12, 0.16 and 0.20; however, broader variation of relative pressures can be used for determination of surface area and especially pore size. That is, if the majority of relative pressure points are between 0.05 and 0.35, one can employ additional relative pressure points which do not correspond to the addition of the adsorptive in successive equal increments.

As noted previously, the temperature of the adsorptive can change slightly due to environmental conditions of the liquid nitrogen bath. More specifically, the temperature of the liquid nitrogen, held in a dewar, always is found to be somewhat different than the normal boiling point, because of dissolved impurities from the atmosphere and because of ambient pressure fluctuations. Dissolved impurities usually increase the bath temperature sufficiently to cause the vapor pressure of pure liquid nitrogen within the sample cell to increase above ambient pressure. The prior art has compensated for this by adding about 15 mm Hg to ambient pressure.

However, according to the present method, the saturation vapor pressure is measured and the correction factor is not used became the saturation vapor pressure thermometer measures the temperature at each point to provide an accurate measurement of the saturation vapor pressure.

Dosing schemes known to those skilled in the art can be used with the present invention. Alternatively, three slightly different dosing methods can be used in this invention. The dosing alternative method employs a philosophy that if the data point is not at the relative pressure point desired, it should be recorded anyway, and the next dose of adsorptive gas should be accurate to obtain the desired relative pressure point. Data required at precise relative pressure points are obtained by interpolating the measured data. Both sets of data (measured and interpolated) are always available to the instrument user. Consequently, all adsorbate doses are equilibrated and recorded. The alternative dosing method does not use any iterative procedure within each data point.

The three alternative dosing methods are: (1) Unknown Mode, (2) Learn Mode and (3) Copy Mode. All of these modes use a target table of relative pressures which are programmed into the scientific instrument. The instrument attempts to record data points at these table values, however a mathematical interpolation is used to report very precise relative pressure values. Additional data points greater than the target number and the use of the interpolation eliminates the need for accurate pressure targeting.

(1) Unknown Mode. This general purpose mode is used to measure unknown samples. Small fixed pressure doses are made at low values of relative pressure. The pressure of these doses is calculated using the measured free space of the sample tube and the assumption that the sample has a minimum surface area. The equilibrated sample pressure and the saturation pressure are recorded for each dose.

After about six small low pressure data points have been measured, it is calculated by methods known to those skilled in the art, an additional amount of gas which must be added in order to achieve the first target relative pressure point. The calculation provide a one-shot single value which might or might not provide the desired outcome.

The maximum system pressure and the manifold volume limits the volume of gas which might be added during each dose. When the calculated amount of gas that should be added to achieve the target point is more gas than the system limit, then two or more fully equilibrated data points are taken.

All data points are recorded even if they are not precisely targeted. This dosing method philosophy can be characterized as try and do better next time. The more data which has been obtained, the better the isotherm can be predicted, so that extra data points are not necessary to be obtained.

It is most often the case that ten or less additional data points are taken when complete adsorption and desorption isotherms are measured. The number of target relative pressure points required for each analysis is determined from the required output data. If only a BET surface area is required, for example, just the first part of the isotherm from 0 to 0.3 relative pressure can be measured.

(2) Learn Mode. This dosing mode obtains a standard isotherm which may be copied one or more times and is useful for precise targeting of required targeting of required relative pressure points and for reduced operating times. The sample measurement throughput is dependent upon many different factors. The total sample measurement period can be considered to comprise the following main sections: outgassing of the sample, setup of the sample measurement conditions, adsorptive dosing time required by the dosing scheme, sample/adsorptive equilibration time, and sample results and post-processing time.

The Learn Mode and Copy Mode have not been used before and is particularly useful for Quality Control (QC) laboratories. A fully detailed analysis is obtained using a fixed table of relative pressures.

This dosing mode is essentially identical to the Unknown Mode, except that the target table of relative pressures are fixed and additional data points are chosen at areas of maximum slope change. The Learn Mode is slower to perform than the Unknown Mode. The isotherm data obtained from this mode is stored in the instrument memory. The isotherm data is very detailed and provides enough information for it to be used as a model for subsequent analysis of the same type of compound for the Copy Mode.

(3) Copy Mode. This mode can only be used when a Learn Mode run has stored an isotherm for a similar sample of the same material. The Copy Mode provides maximum sample throughput for routine quality control analysis. The target values of the relative pressure are chosen based upon the required output data and need not be identical to the stored standard isotherm. Targeted relative pressure points are calculated using the standard isotherm and the weight of the sample being measured. This mode eliminates the need for the low pressure fixed dose points. Only the target table of relative pressure points are employed.

The desorption mode is the reverse of the adsorption mode. The desorption mode employs a solid sample, referred to as the desorbent, the morphological characteristics of which are sought to be determined, and a gas or liquid referred to herein as the desorbate. The desorbate is desorbed from the sample during the desorption mode, the desorbate being thereafter referred to as the desorptive. Therefore, the desorption mode employs a starting sample material, which has been first outgassed as described herein, and then its surface and any pores present are contacted with an adsorptive in a manner sufficient to condense the adsorptive on the sample material, fill the pores, and coat the outer surface of the sample material with at least a monolayer of condensed desorbate. As a matter of convenience, the sample material typically is saturated with an adsorbate to ensure complete filling of the sample pores. Upon the completion of condensing the gas on the sample material, it is referred to as the desorbate. Thus, the terms "desorptive" and "desorbate" are used in place of "adsorptive" and "adsorbate" merely to identify the mode in which the gas or liquid constituting that substance is employed. The materials which can constitute the adsorptive and the desorptive are the same. Like the adsorptive, the desorptive gas can comprise a single component gas and an inert carrier gas. Preferably, the desorptive gas comprises at least 80 percent of a single component gas and less than 20 percent of a carrier gas. Most preferably, the desorptive gas comprises a single gas without a carrier gas.

Accordingly, to conduct the desorption mode, a chamber of known volume and temperature, as described in accordance with the adsorption mode, is provided with a sample having desorbate condensed thereon and in equilibrium with a chamber atmosphere consisting of gaseous desorptive. This typically is performed by conducting the adsorption mode until sample saturation is achieved as described hereinabove.

It is to be understood that the present invention is not limited to any particular mathematical model for using the information embodied in either the adsorption or desorption isotherm, and such information can be manipulated as desired in accordance with any conventional procedure. However, the preferred method to determine the surface area pore volume and pore size distribution is according to the well known principles as described in U.S. Pat. No. 4,489,593 to Pieters, et al. For example, surface area analysis is conducted through determining a number of points which enable a least squares fit of the BET equation to be accomplished.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes can be made by those skilled in the art without departing from the spirit of the invention.

We claim:

1. An apparatus used in measurement of morphological characteristics of a solid sample contained in a vessel comprising:

a means for providing a heat transfer between a cooling liquid and a solid sample contained in a sample vessel, said sample vessel being partially immersed in said liquid and extending above the surface of said cooling liquid, and wherein said means for providing a heat transfer is a heat conductive metallic material which extends from said sample vessel into said cooling liquid, and wherein said means for providing a heat transfer remains below the surface of said cooling liquid without being exposed to the atmosphere during measurement of morphological characteristics of said sample, and provides a stabilized temperature to said sample vessel.

2. The apparatus of claim 1 which further comprises a second means for providing a heat transfer, which is a heat conductive material that extends from a saturation vapor pressure thermometer into said cooling liquid, and said second means for providing a heat transfer which remains below the surface of said cooling liquid during said measurement of morphological characteristics of said sample, and wherein the second means for providing a heat transfer is apart from said means for heat transfer which extends from said sample vessel.

3. The apparatus of claim 1 wherein a first portion of said means for providing a heat transfer is attached to a saturation vapor pressure thermometer and a second portion of said means for providing a heat transfer is attached to said sample vessel to provide a uniform temperature between said thermometer and said sample vessel.

4. The apparatus of claim 3 wherein said first end of said means for providing a heat transfer comprises a first collar to insert said sample vessel, said first collar extending around said sample vessel, and said second end of said means for providing a heat transfer comprises a second collar to insert said saturation vapor pressure thermometer, said second collar extending around said saturation vapor pressure thermometer.

5. The apparatus of claim 1 wherein said means for providing a heat transfer is constructed of an element selected from the group consisting of copper, silver, gold and alloys of steel and brass.

6. The apparatus of claim 5 wherein said means for providing a heat transfer contains comprises a braided heat conductive material.

7. The apparatus of claim 5 wherein said means for providing a heat transfer comprises a heat conductive material wound around said sample vessel.

8. A method of determining a sorption isotherm comprising the steps of:

a) inserting a sample to be analyzed into a sample vessel and inserting said sample vessel into a container of volatile cooling liquid, wherein a portion of said sample vessel extends above the surface of said cooling liquid and, said sample vessel contains an exterior metallic means that extends from said sample vessel and remains below the surface of said cooling liquid during analysis of said sample, said means providing a heat transfer between said cooling liquid and said sample vessel and further providing a stabilized temperature to said sample vessel;

b) dosing an amount of adsorbent gas to said sample; and c) constructing a sorption isotherm resulting from the amount of said adsorptive gas that is condensed on said sample.

9. The method of claim 8, which further comprises determining the amount of said absorbent gas that is to be dosed to said sample from a previously measured sorption measurement of a sample that has the same composition as the sample being analyzed.

10. The method of claim 9, which further comprises measuring the temperature of said cooling liquid with a saturation vapor pressure thermometer after dosing an amount of adsorbent gas to said sample.

11. The method of claim 10, wherein said saturation vapor pressure thermometer contains an exterior means for providing a heat transfer which extends from said saturation vapor pressure thermometer into said cooling liquid and remains below the surface of said cooling liquid during analysis of said sample, said means for providing a heat transfer providing a heat transfer between said cooling liquid and said vapor pressure thermometer and further providing a stabilized temperature to said thermometer.

12. The method of claim 11, wherein said external means for providing a heat transfer on said vessel and external means for providing a heat transfer on said saturation vapor pressure thermometer provides a thermal bridge between said vessel and said thermometer to provide a uniform temperature between said vessel and said thermometer.

* * * * *